US012810968B2

(12) United States Patent
Katsuta et al.

(10) Patent No.: US 12,810,968 B2
(45) Date of Patent: Nov. 24, 2026

(54) SIMULATION METHOD, STORAGE MEDIUM, SIMULATION APPARATUS, FILM FORMING APPARATUS, AND METHOD OF MANUFACTURING ARTICLE

(71) Applicant: CANON KABUSHIKI KAISHA, Tokyo (JP)

(72) Inventors: Ken Katsuta, Saitama (JP); Yuichiro Oguchi, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 1171 days.

(21) Appl. No.: 17/679,364

(22) Filed: Feb. 24, 2022

(65) Prior Publication Data

US 2022/0284992 A1 Sep. 8, 2022

(30) Foreign Application Priority Data

Mar. 2, 2021 (JP) ................................ 2021-032586
Dec. 10, 2021 (JP) ................................ 2021-201174

(51) Int. Cl.
*G16C 20/30* (2019.01)
*C08J 5/18* (2006.01)
(Continued)

(52) U.S. Cl.
CPC ................ *G16C 20/30* (2019.02); *C08J 5/18* (2013.01); *G03F 7/0002* (2013.01); *G06F 30/20* (2020.01);
(Continued)

(58) Field of Classification Search
CPC .......... G16C 20/30; C08J 5/18; G03F 7/0002; G06F 30/20; G06F 30/25; G06F 2111/04; G06F 2113/08
See application file for complete search history.

(56) References Cited

U.S. PATENT DOCUMENTS 7,157,036 B2 * 1/2007 Choi ...................... B82Y 10/00 264/300
8,512,797 B2 * 8/2013 Schumaker ........... G03F 7/0002 427/256

(Continued)

FOREIGN PATENT DOCUMENTS

JP 2012212833 A 11/2012
JP 2013104751 A 5/2013

(Continued)

OTHER PUBLICATIONS

Nguyen, H., Burkardt, J., Gunzburger, M., Ju, L., and Saka, Y., "Constrained CVT meshes and a comparison of triangular mesh generators", 2009, Computational Geometry: Theory and Applications, vol. 42, pp. 1-19 (Year: 2009).*

(Continued)

*Primary Examiner* — Emerson C Puente
*Assistant Examiner* — Emily Gorman Leathers
(74) *Attorney, Agent, or Firm* — ROSSI, KIMMS & McDOWELL LLP

(57) ABSTRACT

The present invention provides a simulation method of predicting a behavior of a curable composition in a process of bringing a second member into contact with a plurality of droplets of the curable composition arranged on a first member and forming a film of the curable composition on the first member, the method comprising: determining a volume used for predicting the behavior with respect to each of a plurality of specific droplets which are arranged inside a prediction target region for predicting the behavior, among the plurality of droplets, based on an index indicating a positional relationship between a boundary of the prediction target region and each specific droplet; and predicting the behavior of the curable composition inside the prediction (Continued)

target region based on the volume determined with respect to each of the plurality of specific droplets.

5 Claims, 9 Drawing Sheets

(51) Int. Cl.

| | |
|---|---|
| ***G03F 7/00*** | (2006.01) |
| ***G06F 30/20*** | (2020.01) |
| ***G06F 30/25*** | (2020.01) |
| ***G06F 111/04*** | (2020.01) |
| ***G06F 113/08*** | (2020.01) |

(52) U.S. Cl.
CPC .......... *G06F 30/25* (2020.01); *G06F 2111/04* (2020.01); *G06F 2113/08* (2020.01)

(56) References Cited

U.S. PATENT DOCUMENTS 8,586,126 B2 * 11/2013 Schumaker ............ B82Y 40/00 427/256
10,663,869 B2 * 5/2020 Khusnatdinov ..... G03F 7/70116
2005/0187339 A1 * 8/2005 Xu ........................ G03F 7/0002 524/556
2009/0014917 A1 * 1/2009 Hodge ................... B82Y 10/00 264/401
2021/0350047 A1 11/2021 Asano

FOREIGN PATENT DOCUMENTS

JP 2020123719 A * 8/2020 ........... G03F 7/0002
JP 2020205416 A 12/2020

OTHER PUBLICATIONS

Ghaffari, M., and Xiao, S., “Smoothed Particle Hydrodynamics with Stress Points and Centroid Voronoi Tessellation (CVT) Topology Optimization”, 2016, International Journal of Computational Methods, vol. 13, No. 6 (Year: 2016).*
Lopez, J., Hernandez, J., Gomez, P., and Faura, F., “VOFTools—A software package of calculation tools for volume of fluid methods using general convex grids”, 2018, Computer Physics Communications, vol. 223, pp. 45-54, doi.org/10.1016/j.cpc.2017.09.032 (Year: 2018).*

* cited by examiner

SIMULATION METHOD, STORAGE MEDIUM, SIMULATION APPARATUS, FILM FORMING APPARATUS, AND METHOD OF MANUFACTURING ARTICLE

BACKGROUND OF THE INVENTION

Field of the Invention

The present invention relates to a simulation method, a storage medium, a simulation apparatus, a film forming apparatus, and a method of manufacturing an article.

Description of the Related ART

There is known a film forming method of forming a film formed from a cured product of a curable composition on a substrate by arranging the curable composition on the substrate, bringing the curable composition and a mold into contact with each other, and curing the curable composition. Such a film forming method can be applied to an imprint method and a planarization method. The imprint method uses a mold having a pattern and cures a curable composition on a substrate while the curable composition is in contact with the mold, thereby transferring the mold pattern onto the curable composition on the substrate. The planarization method uses a mold having a flat surface and forms a film having a flat upper surface by curing a curable composition on a substrate while the curable composition is in contact with the flat surface.

A curable composition is arranged in the form of a plurality of droplets on a substrate. Subsequently, a mold can be pressed against the plurality of droplets of the curable composition. This spreads the plurality of droplets on the substrate and forms a film of the curable composition. In such a process, for example, it is important to form a film of a curable composition having a uniform thickness and to include no air bubbles in the film. In order to achieve such requirements, it is possible to adjust the arrangement of a plurality of droplets of a curable composition, a method of pressing a mold against the plurality of droplets of the curable composition, conditions for the method, and the like. However, enormous time and cost are required to implement such adjustment by trial and error using a film forming apparatus (an imprint apparatus and a planarization apparatus). Accordingly, there are demands for the use of simulation for supporting such adjustment.

Japanese Patent Laid-Open No. 2020-123719 discloses a simulation method for predicting the behavior of a curable composition arranged on a substrate (first member) in a process of bringing a mold (second member) into contact with a plurality of droplets of the curable composition on the substrate and forming a film of the curable composition. This simulation method defines a computational grid constituted by a plurality of computational elements so as to make a plurality of droplets of the curable composition converge into one computational element and obtains the behavior of the curable composition in each computational element using a model corresponding to the state of the curable composition in each computational element. This makes it possible to speed up the computation.

Simulation methods of predicting the behavior of a curable composition include a computation method including extracting, as a prediction target region, a part (partial region) of the region of a substrate on which a plurality of droplets of the curable composition are arranged and predicting the behavior of the curable composition inside the prediction target region. This computation method can reduce the computation cost (computation time, computation load, and the like) as compared with the case of predicting the behavior of a curable composition in the entire region on a substrate on which a plurality of droplets of the curable composition are arranged. However, this computation method sometimes obtains a computation result (prediction result) that leads to false recognition by the user, such as local increases and decreases in the film thickness of a curable composition near, for example, a boundary of a prediction target region depending on a computation model for such boundary.

SUMMARY OF THE INVENTION

The present invention provides, for example, a technique advantageous in reducing false recognition by the user concerning the prediction result of the behavior of a curable composition inside a prediction target region.

According to one aspect of the present invention, there is provided a simulation method of predicting a behavior of a curable composition in a process of bringing a second member into contact with a plurality of droplets of the curable composition arranged on a first member and forming a film of the curable composition on the first member, the method comprising: determining a volume used for predicting the behavior with respect to each of a plurality of specific droplets which are arranged inside a prediction target region for predicting the behavior, among the plurality of droplets, based on an index indicating a positional relationship between a boundary of the prediction target region and each specific droplet; and predicting the behavior of the curable composition inside the prediction target region based on the volume determined with respect to each of the plurality of specific droplets.

Further features of the present invention will become apparent from the following description of exemplary embodiments with reference to the attached drawings.

DESCRIPTION OF THE EMBODIMENTS

Figure 1:
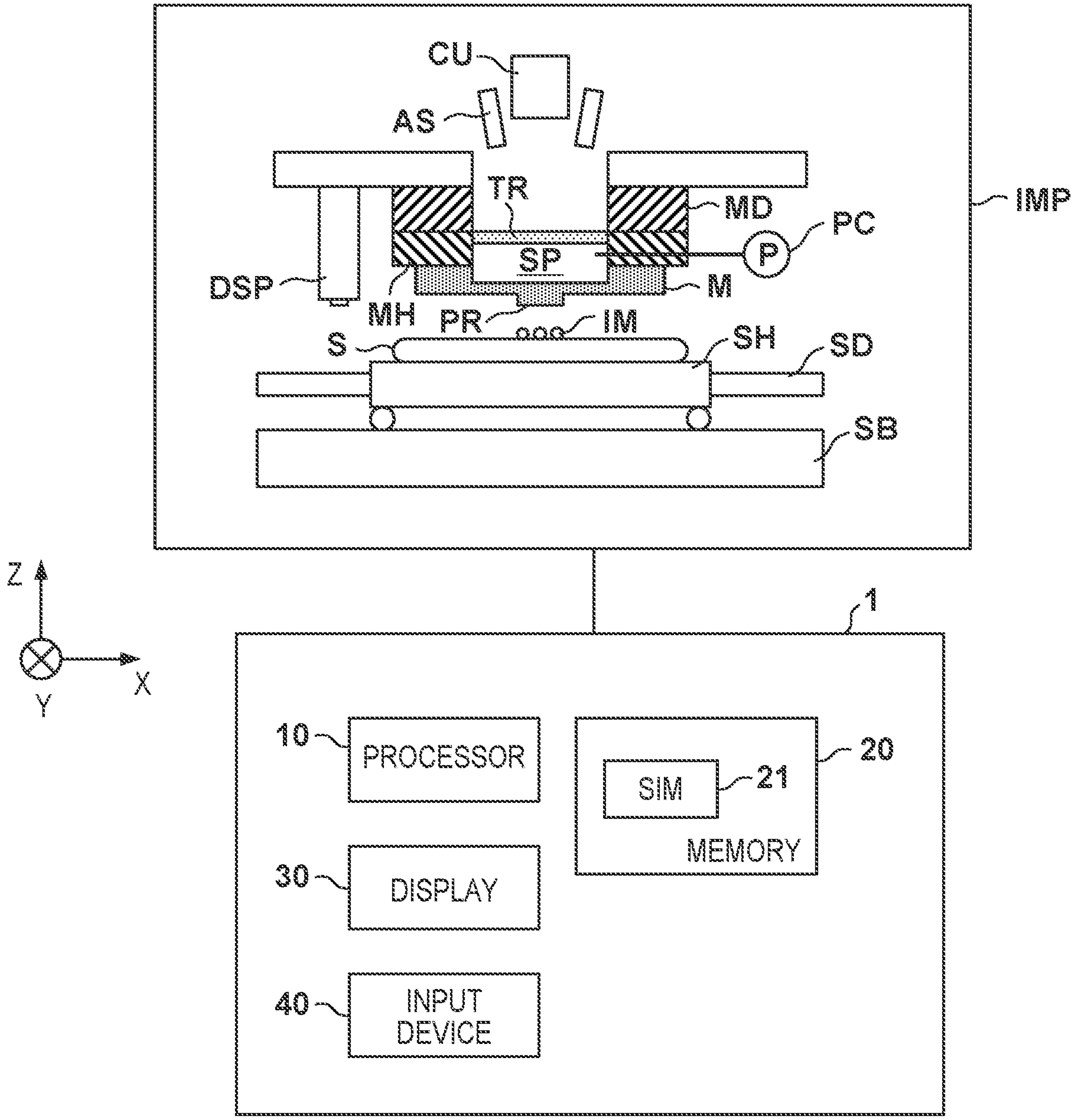
FIG. 1 is a schematic view showing the arrangement of a system including a film forming apparatus and an information processing apparatus.

Hereinafter, embodiments will be described in detail with reference to the attached drawings. Note, the following embodiments are not intended to limit the scope of the claimed invention. Multiple features are described in the embodiments, but limitation is not made an invention that requires all such features, and multiple such features may be combined as appropriate. Furthermore, in the attached drawings, the same reference numerals are given to the same or similar configurations, and redundant description thereof is omitted.

First Embodiment

The first embodiment of the present invention will be described. FIG. 1 is a schematic view showing the arrangement of a system including a film forming apparatus IMP and an information processing apparatus 1 according to this embodiment. The film forming apparatus IMP executes a process (to be sometimes referred to as a film forming process hereinafter) of bringing a plurality of droplets of a curable composition IM arranged on a substrate S (first member) and a mold M (second member) into contact with each other and forming a film of the curable composition IM in a space between the substrate S and the mold M. The film forming apparatus IMP may be formed as, for example, an imprint apparatus or a planarization apparatus. In this case, the substrate S and the mold M are interchangeable, and a film of the curable composition IM may be formed in the space between the mold M and the substrate S by bringing a plurality of droplets of the curable composition IM arranged on the mold M and the substrate S into contact with each other. That is, the first member may serve as the substrate S and the second member may serve as the mold M, or the first member may serve as the mold M and the second member may serve as the substrate S.

The imprint apparatus performs an imprint process, as a film forming process, which uses the mold M having a pattern to transfer the pattern of the mold M to the curable composition IM on the substrate S. The imprint apparatus uses the mold M having a pattern region PR provided with a pattern. In the print process, the imprint apparatus brings the curable composition IM on the substrate S and the pattern region PR of the mold M into contact with each other, fills, with the curable composition IM, a space between the mold M and a region where the pattern of the substrate S is to be formed, and then cures the curable composition IM. This transfers the pattern of the pattern region PR of the mold M to the curable composition IM on the substrate S. For example, the imprint apparatus forms a pattern made of a cured product of the curable composition IM on each of a plurality of shot regions of the substrate S.

The planarization apparatus performs a planarization process, as a film forming process, which planarizes the curable composition IM on the substrate S by using the mold M having a flat surface. In the planarization process, the planarization apparatus brings the curable composition IM on the substrate S and the flat surface of the mold M into contact with each other and cures the curable composition IM, thereby forming a film having a flat upper surface on the substrate. When using the mold M having dimensions (size) that cover the entire region of the substrate S, the planarization apparatus forms a film made of a cured product of the curable composition IM on the entire region of the substrate S.

As the curable composition, a material to be cured by receiving curing energy can be used. As the curing energy, an electromagnetic wave, heat, or the like can be used. The electromagnetic wave can include, for example, light selected from the wavelength range of 10 nm (inclusive) to 1 mm (inclusive) and, more specifically, infrared light, a visible light beam, or ultraviolet light. The curable composition can be a composition cured by light irradiation or heating. A photo-curable composition cured by light irradiation contains at least a polymerizable compound and a photopolymerization initiator and may further contain a nonpolymerizable compound or a solvent, as needed. The nonpolymerizable compound is at least one material selected from the group consisting of a sensitizer, a hydrogen donor, an internal mold release agent, a surfactant, an antioxidant, and a polymer component. The viscosity (the viscosity at 25° C.) of the curable composition can be, for example, 1 mPa·s (inclusive) to 100 mPa·s (inclusive). As the material of the substrate, for example, glass, a ceramic, a metal, a semiconductor, a resin, or the like can be used. A member made of a material different from the substrate may be provided on the surface of the substrate S, as needed. The substrate S includes, for example, a silicon wafer, a compound semiconductor wafer, or silica glass.

In the specification and the accompanying drawings, directions will be indicated on an XYZ coordinate system in which directions parallel to the surface of the substrate S are defined as the X-Y plane. Directions parallel to the X-axis, the Y-axis, and the Z-axis of the XYZ coordinate system are the X direction, the Y direction, and the Z direction, respectively. A rotation about the X-axis, a rotation about the Y-axis, and a rotation about the Z-axis are θX, θY, and θZ, respectively. Control or driving concerning the X-axis, the Y-axis, and the Z-axis means control or driving concerning a direction parallel to the X-axis, a direction parallel to the Y-axis, and a direction parallel to the Z-axis, respectively. In addition, control or driving concerning the θX-axis, the θY-axis, and the θZ-axis means control or driving concerning a rotation about an axis parallel to the X-axis, a rotation about an axis parallel to the Y-axis, and a rotation about an axis parallel to the Z-axis, respectively. In addition, a position is information that can be specified based on coordinates on the X-, Y-, and Z-axes, and an orientation is information that can be specified by values on the θX-, θY-, and θZ-axes. Alignment means controlling the position and/or orientation.

The film forming apparatus IMP includes a substrate holder SH that holds the substrate S, a substrate driving mechanism SD that drives (moves) the substrate S by driving the substrate holder SH, and a support base SB that supports the substrate driving mechanism SD. In addition, the film forming apparatus IMP includes a mold holder MEI that holds the mold M and a mold driving mechanism MD that drives (moves) the mold M by driving the mold holder MH.

The substrate driving mechanism SD and the mold driving mechanism MD drive at least one of the substrate S and the mold M so as to adjust the relative position between the substrate S and the mold M. That is, the substrate driving mechanism SD and the mold driving mechanism MD form a relative driving mechanism that relatively drives the substrate S and the mold M. Adjustment of the relative position between the substrate S and the mold M by the relative driving mechanism includes driving to bring the curable composition IM on the substrate S and the mold M into contact with each other and driving to separate the mold M from the cured curable composition IM on the substrate S. In addition, adjustment of the relative position between the substrate S and the mold M by the relative driving mechanism includes aligning between the substrate S and the mold M. The substrate driving mechanism SD is configured to drive the substrate S with respect to a plurality of axes (for example, three axes including the X-axis, Y-axis, and θZ-axis, and preferably six axes including the X-axis, Y-axis, Z-axis, θX-axis, θY-axis, and θZ-axis). The mold driving mechanism MD is configured to drive the mold M with respect to a plurality of axes (for example, three axes including the Z-axis, θX-axis, and θY-axis, and preferably six axes including the X-axis, Y-axis, Z-axis, θX-axis, θY-axis, and θZ-axis).

The film forming apparatus IMP includes a curing unit CU for curing the curable composition IM with which the space between the substrate S and the mold M is filled. The curing unit CU cures the curable composition IM on the substrate S by applying curing energy to the curable composition IM through the mold M. The film forming apparatus IMP has a transparent member TR for forming a space SP on the back surface side of the mold M (the side opposite to the surface facing the substrate S). The transparent member TR is made of a material that transmits curing energy from the curing unit CU. This makes it possible to apply curing energy to the curable composition IM on the substrate S. In addition, the film forming apparatus IMP includes a pressure control unit PC that controls the deformation of the mold M in the Z-axis direction by controlling the pressure of the space SP. For example, the pressure control unit PC increases the pressure of the space SP to a pressure higher than the atmospheric pressure to deform the substrate S to a convex shape. As the pressure control unit PC brings the mold M into contact with the curable composition IM on the substrate while controlling the deformation of the mold M, the contact area between the mold M and the curable composition IM on the substrate gradually increases. This can reduce air bubbles left in the curable composition IM between the mold M and the substrate S.

The film forming apparatus IMP includes a dispenser DSP for arranging, supplying, or distributing the curable composition IM on the substrate S. The substrate S on which the curable composition IM is arranged may be supplied (loaded) to the film forming apparatus IMP. In this case, the dispenser DSP may not be provided for the film forming apparatus IMP. The film forming apparatus IMP may include an alignment scope AS for measuring the misalignment (alignment error) between the substrate S (or a shot region of the substrate S) and the mold M.

The information processing apparatus 1 executes a computation to predict the behavior of the curable composition IM in the film forming process executed by the film forming apparatus IMP. The information processing apparatus 1 may be understood as a simulation apparatus that predicts the behavior of the curable composition IM in a film forming process. More specifically, the information processing apparatus 1 executes a computation to predict the behavior of the curable composition IM in the film forming process of bringing the mold M into contact with a plurality of droplets of the curable composition IM arranged on the substrate S and forming a film of the curable composition IM in the space between the substrate S and the mold M.

The information processing apparatus 1 is implemented by, for example, incorporating a simulation program 21 in a general-purpose or dedicated computer. Alternatively, the information processing apparatus 1 may be implemented by a PLD (Programmable Logic Device) such as an FPGA (Field Programmable Gate Array) or an ASIC (Application Specific Integrated Circuit). In this embodiment, the information processing apparatus 1 is implemented by a computer including a processor 10, a memory 20, a display 30 (display unit), and an input device 40 (input unit). The memory 20 stores the simulation program 21 for predicting the behavior of the curable composition IM in a film forming process. The processor 10 can perform a simulation to predict the behavior of the curable composition IM in the film forming process by reading out and executing the simulation program 21 stored in the memory 20. Note that the memory 20 may be a semiconductor memory, a disk such as a hard disk, or a memory in another form. The simulation program 21 may be stored in a memory medium that can be read-accessed by a computer or provided for the information processing apparatus 1 via communication facilities such as an electric communication line.

Figure 2:
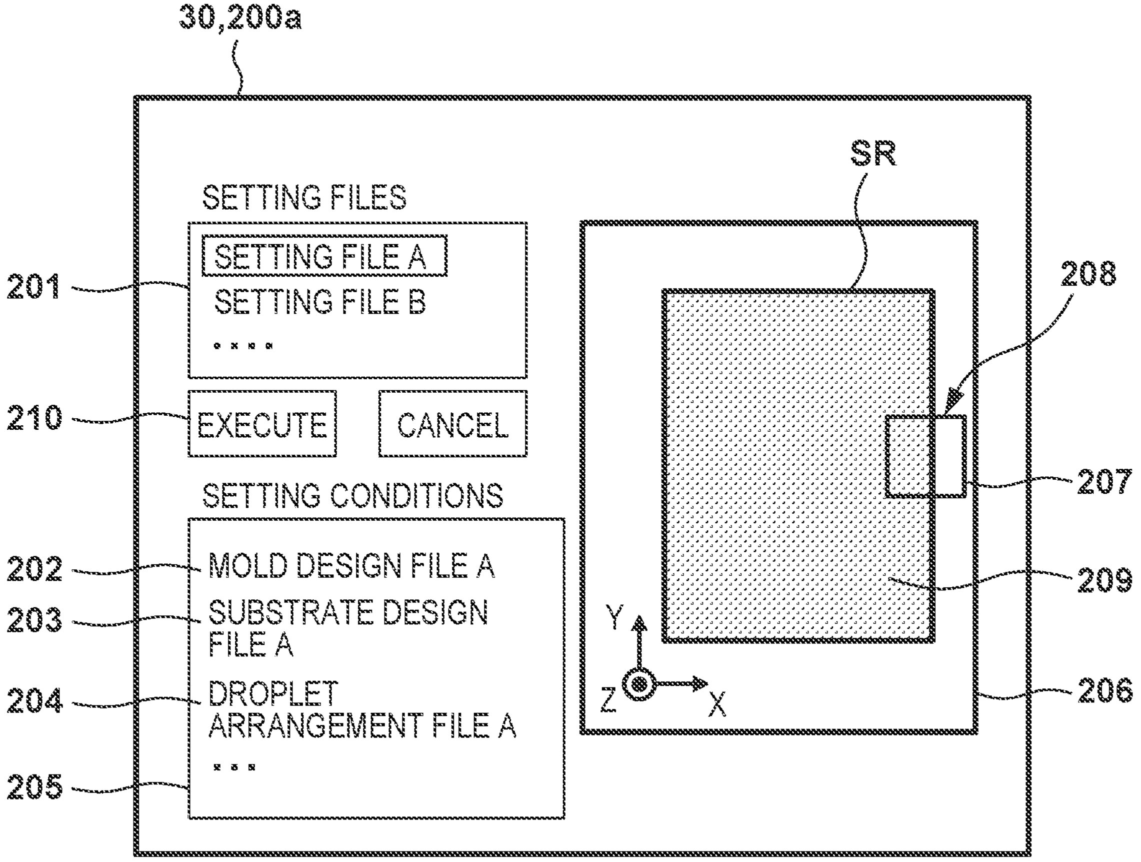
FIG. 2 is a view showing a setting screen for setting simulation conditions.

FIG. 2 shows a setting screen 200*a* for setting simulation conditions, which serves as a user interface displayed (provided) on the display 30 of the information processing apparatus 1 when the simulation program 21 according to this embodiment is executed (activated). In the embodiment, as shown in FIG. 2, the user can set conditions for a simulation for predicting the behavior of the curable composition IM by inputting necessary information via the input device 40 while referring to the user interface provided on the display 30.

For example, as shown in FIG. 2, a plurality of types of setting files 201 (a setting file A and a setting file B) in which simulation conditions are set can be created in advance and stored in the memory 20. In this case, the user can select the setting file 201 corresponding to desired simulation conditions from a plurality of types of setting files 201. Simulation conditions are conditions that are set to predict the behavior of the curable composition IM in a film forming process and may be understood as conditions at the time of execution of an imprint process (for example, conditions (information) concerning the pattern of the mold M and the volume and arrangement of a plurality of droplets discharged). The setting files 201 are also files for integrating and managing conditions for an imprint process for the execution of a simulation. The setting files 201 can include, as simulation conditions, a mold design file 202 including the design information of the mold M, a substrate design file 203 including the design information of the substrate S, and a droplet arrangement file 204 indicating the volume and arrangement of a plurality of discharged droplets of the curable composition IM.

The plurality of files 202 to 204 included in the setting files 201 are stored in the memory 20 in advance. Storing the plurality of files 202 to 204 in the memory 20 in the form of a library in this manner makes it easy to set simulation conditions (analysis conditions). The file names of the plurality of files 202 to 204 included in the setting files 201 can be displayed on a condition display window 205 of the setting screen 200*a* shown in FIG. 2. In addition, a visual window 206 of the setting screen 200*a* displays the image information stipulated in the setting files 201 to prevent the incorrect input of the setting files 201. For example, as shown in FIG. 2, the image information can include the information of an image indicating the arrangement of a plurality of droplets 209 of the curable composition IM arranged on one shot region SR on the substrate S (that is, a region of the substrate S which corresponds to the pattern region PR of the mold M).

For the sake of simplicity, this embodiment exemplifies three files (the mold design file 202, the substrate design file 203, and the droplet arrangement file 204) as simulation condition files included in the setting files 201. Note, however, that files may be created concerning simulation conditions that are not described in this embodiment and may be stored in the memory 20 in the form of a library. For example, the following information may be set as simulation conditions in the setting files 201: information concerning an imprint process such as the force (pressing force) that presses the mold M against the curable composition IM on the substrate S and the time (filling time) during which the mold M is pressed against the curable composition IM.

In this case, as indicated by the setting screen 200*a* in FIG. 2 (visual window 206), a prediction target region 207 in which the behavior of the curable composition IM in a film forming process is predicted can be set in the setting files 201. The prediction target region 207 is a region for which the prediction (that is, simulation and computation) of the behavior of a curable composition in a film forming process is to be performed and can be set in a part (partial region) of the shot region SR on the substrate S. Predicting the behavior of the curable composition IM only within the prediction target region 207 in this manner can reduce the computation cost (computation time, computation load, and the like) as compared with the case in which the behavior of the curable composition IM is predicted concerning the entire shot region SR. That is, this can obtain a simulation result in a short period of time.

In this embodiment, as shown in FIG. 2, the prediction target region 207 is defined as a rectangular region with a side parallel to the X-axis and the Y-axis in the XYZ coordinate system being a boundary 208 (edge). The dimensions and position of the prediction target region 207 in the XYZ coordinate system are defined in the setting files 201. For example, the dimensions and position of the prediction target region 207 in the setting files 201 can be defined by the minimum and maximum values in the X-direction coordinates and the minimum and maximum values in the Y-direction coordinates of the prediction target region 207 when the center of the shot region SR is set as an origin. Note that, in this embodiment, the prediction target region 207 is defined as a rectangular region. However, this is not exhaustive, and this region may be defined as a region having a different shape.

The visual window 206 shown in FIG. 2 displays one shot region SR of the substrate S and the arrangement of the plurality of droplets 209 of the curable composition IM stipulated by the droplet arrangement file 204. The visual window 206 also displays the prediction target region 207 for the prediction of the behavior of the curable composition IM (the plurality of droplets 209) in a film forming process. Configuring the setting screen 200*a* on the display 30 in this manner allows the user (operator) to visually check simulation conditions and the position and dimensions of the prediction target region 207. This makes it possible to reduce file selection errors and incorrect input of simulation conditions by the user. When executing a simulation, the user checks the information displayed on the condition display window 205 and the visual window 206 and operates an execution button 210 if there is no problem in the information. This makes it possible to execute a computation process (simulation computation) for predicting the behavior of the curable composition IM (the plurality of droplets 209) inside the prediction target region 207. The simulation result obtained by the simulation computation can be stored in the memory 20.

Although the scheme of setting simulation conditions by selecting the setting files 201 has been described above, the present invention is not limited to this. For example, the present invention may include a scheme of letting the user directly set simulation conditions with respect the user interface (GUI) for input displayed on the display 30 using the input device 40.

Figure 3:
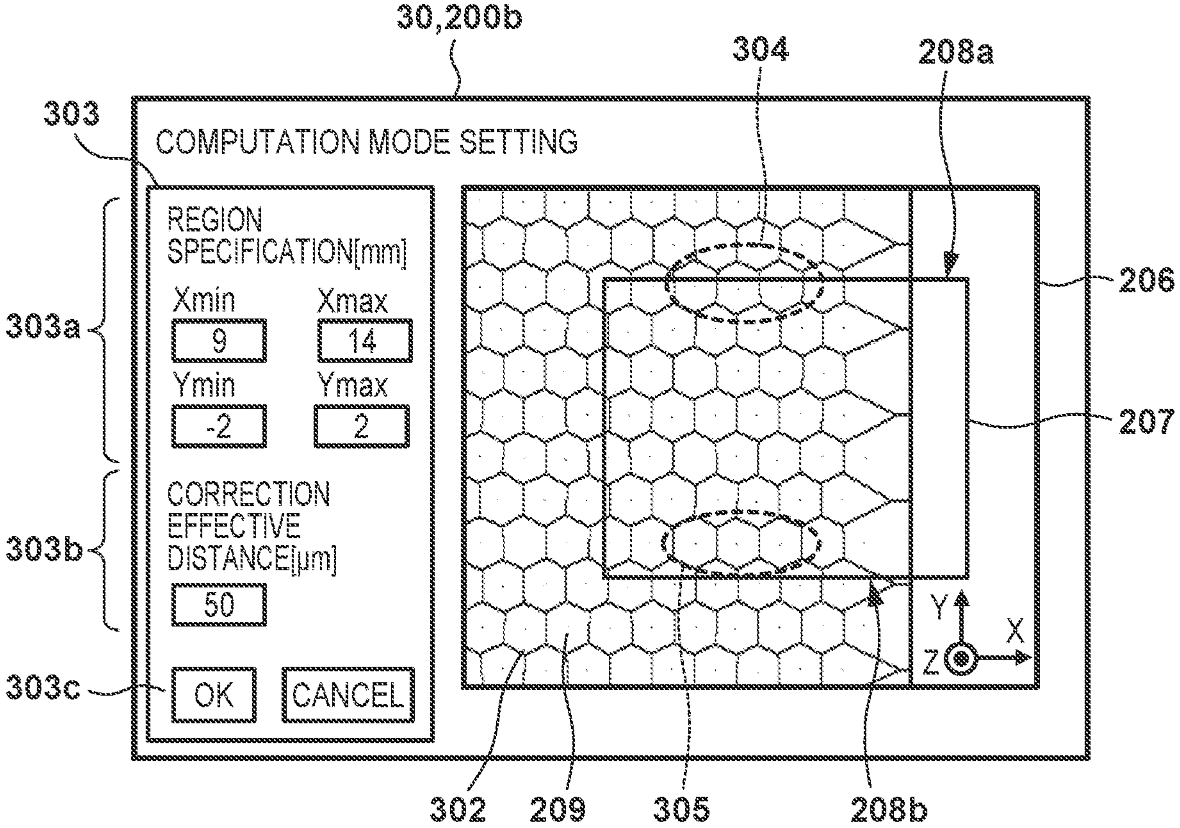
FIG. 3 is a view showing a setting screen for setting simulation conditions.

FIG. 3 shows a setting screen 200*b* for setting simulation conditions as another example of the user interface displayed (provided) on the display 30. The setting screen 200*b* shown in FIG. 3 is provided with an input window 303 for letting the user set the prediction target region 207 via the input device 40. For example, the user inputs, via the input device 40 to an input field 303*a* of the input window 303, the minimum and maximum values of the X-direction coordinates and the minimum and maximum values of the Y-direction coordinates of the prediction target region 207 when the center of the shot region SR serves as an origin. This allows the user to set the position and dimensions of the prediction target region 207. The position and dimensions of the prediction target region 207 set by the user are displayed on the visual window 206. When executing a simulation, the user checks the information displayed on the visual window 206 and operates an OK button 303*c* if there is no problem in the information. This makes it possible to execute a computation process (simulation computation) for predicting the behavior of the curable composition IM (the plurality of droplets 209) inside the prediction target region 207. The simulation result obtained by the simulation computation can be stored in the memory 20.

The input window 303 can be provided with an input field 303*b* for setting a correction effective distance. A correction effective distance defines the distance from the boundary 208 of the prediction target region 207 so as to define a target range for the correction of the volume of the droplet 209 as described later and may be understood as a correction target range. More specifically, of the plurality of droplets 209 (the plurality of specific droplets) arranged inside the prediction target region 207, the droplets 209 at distances from the boundary 208 of the prediction target region 207 which are less than the correction effective distance can be subjected to the correction of the volumes of the droplets.

[Simulation Method]

A simulation method of predicting the behavior of the curable composition IM in a film forming process will be described next. As described above, the simulation method according to this embodiment can extract (cut out) the prediction target region 207 and compute (predict) the behavior of the curable composition IM (the plurality of droplets 209) inside the prediction target region 207. In this case, however, this method may obtain a simulation result that leads to false recognition by the user, for example, local increases/decreases in the film thickness (droplet density) of the curable composition IM near the boundary 208, due to a computation model for the boundary 208 of the prediction target region 207. In this embodiment, as a computation model for the boundary 208 of the prediction target region 207, a model can be applied which performs a computation assuming that each of the plurality of droplets 209 does not spread outward the prediction target region 207 in a film forming process. More specifically, as the computation model, a model (symmetric boundary) can be applied which performs a computation assuming that the spread of the droplets 209 outward the prediction target region 207 is reversed at the boundary 208 of the prediction target region 207, and the droplets 209 spread inward the prediction target region 207.

Accordingly, the simulation method according to this embodiment determines (corrects) the volume of each of the plurality of specific droplets 209 arranged inside the prediction target region 207 among the plurality of droplets 209 arranged on the shot region SR to predict the behavior of the curable composition IM. The volume of each of the plurality of specific droplets 209 can be determined based on an index indicating the positional relationship between the boundary 208 of the prediction target region 207 and each specific droplet 209. The behavior of the curable composition IM (the plurality of specific droplets 209) inside the prediction target region 207 is predicted based on the determined (corrected) volume of each of the plurality of specific droplets 209. This makes it possible to reduce the frequency of obtaining a simulation result (prediction result) that leads to false recognition by the user, for example, local increases/decreases in the film thickness of the curable composition IM near the boundary 208.

Figure 4:
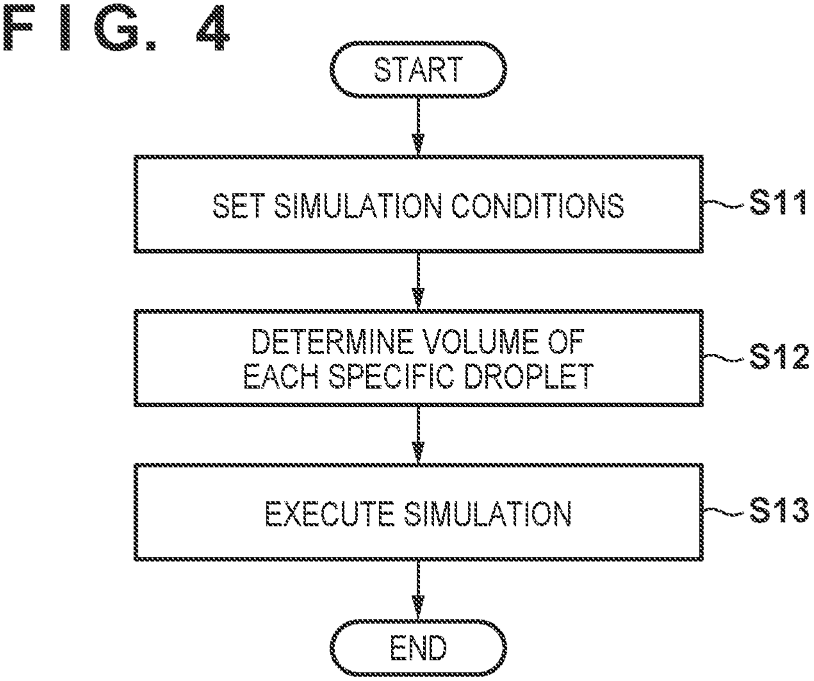
FIG. 4 is a flowchart showing a simulation method.

FIG. 4 is a flowchart showing the simulation method according to this embodiment. The information processing apparatus 1 (processor 10) can execute each step of the flowchart in FIG. 4.

In step S11, the information processing apparatus 1 sets simulation conditions. Simulation conditions can be set by selecting the setting files 201 as described with reference to FIG. 2. In step S12, the information processing apparatus 1 determines the volume of each of the plurality of specific droplets 209 arranged inside the prediction target region 207 based on an index indicating the positional relationship between the boundary 208 of the prediction target region 207 and each specific droplet 209. A detailed method of determining the volume of each specific droplet 209 will be described later. Note that an "index indicating the positional relationship between the boundary 208 of the prediction target region 207 and each specific droplet 209" will be sometimes simply referred to as an "index" hereinafter.

In step S13, the information processing apparatus 1 executes a simulation to predict the behavior of the curable composition IM (the plurality of specific droplets 209) inside the prediction target region 207 in the film forming process. The simulation in step S13 can be executed based on the volume of each specific droplet 209 determined in step S12. For example, the computation technique disclosed in Patent Literature 1 (Japanese Patent Laid-Open No. 2020-123719) can be applied to the simulation in step S13.

[Method of Determining Volume of Each Specific Droplet]

Figure 5:
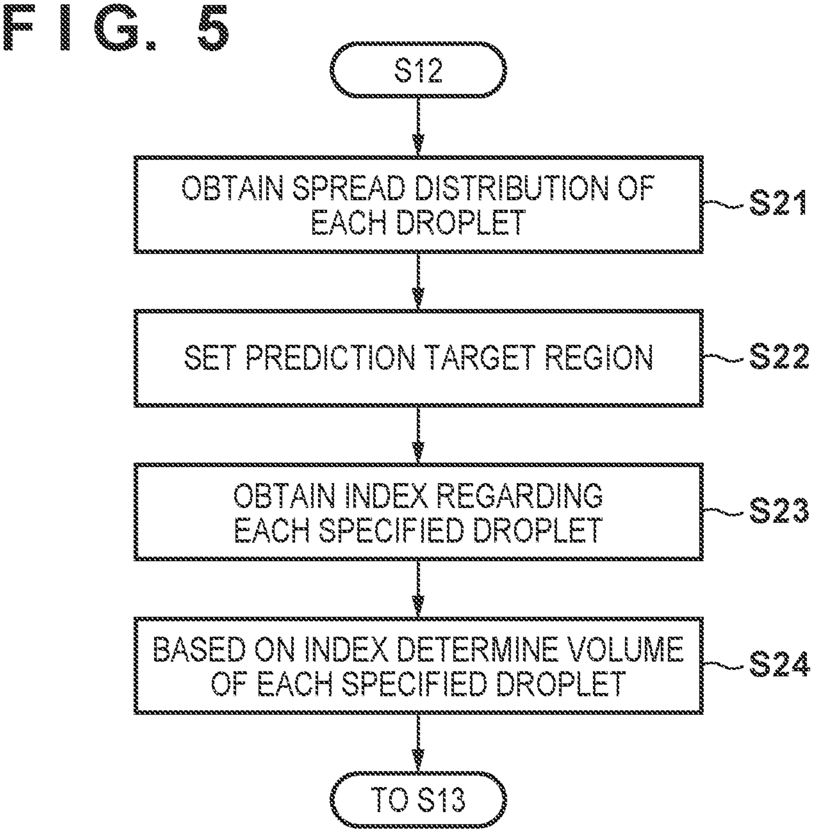
FIG. 5 is a flowchart showing a method of determining the volume of each specific droplet.

A method of determining the volume of each specific droplet 209 which is executed in step S12 will be described next with reference to FIG. 5. FIG. 5 is a flowchart showing the method of determining the volume of each specific droplet 209. This embodiment will exemplify a case in which the volume of each specific droplet 209 is determined by using, as an index, the positional relationship between a distribution (to be sometimes referred to as a spread distribution hereinafter) indicating the tentative spread of droplets in a film forming process and the boundary of the prediction target region 207.

In step S21, the information processing apparatus 1 obtains a distribution (spread distribution) indicating a tentative spread in a film forming process with respect to each of the plurality of droplets 209 arranged on the shot region SR. This embodiment can use, as a spread distribution 302, a unit cell (Voronoi cell) in a Voronoi diagram obtained by segmenting the prediction target region 207 using each of the plurality of droplets 209 arranged on the shot region SR as a generatrix. Note that since step S21 can be executed by a simple computation, the computation cost (especially the computation cost) in step S21 is smaller than the computation cost in the simulation in step S13 described above.

A Voronoi diagram is calculated by segmentation based on which one of a plurality of points (generatrixes) arranged at arbitrary positions in a given distance space each of other points in the same distance space is near, and each segmented region (unit cell) is called a Voronoi cell. As shown in FIG. 3, the calculated Voronoi diagram can be displayed on the visual window 206 of the setting screen 200*b*. In this embodiment, a generatrix is set at the central coordinates of each droplet 209, and a Voronoi cell is calculated as the spread distribution 302. The spread distribution 302 (Voronoi cell) described above can be calculated (created) for each of the plurality of droplets 209 arranged on the shot region SR. Note that the visual window 206 in FIG. 3 displays the prediction target region 207 and a Voronoi diagram concerning the plurality of droplets 209 arranged near the prediction target region 207.

In step S22, the information processing apparatus 1 sets the prediction target region 207. The prediction target region 207 can be set by user input via the input device 40, as shown in, for example, FIG. 3. As shown in FIG. 3, displaying the Voronoi diagram on the visual window 206 allows the user to adjust the position and dimensions of the prediction target region 207 by adjusting the values input to the input field 303*a* while referring to the Voronoi diagram. The visual window 206 allows the user to visually check the boundary 208 of the prediction target region 207, and hence it is possible to prevent the incorrect input of the prediction target region 207. Note that this scheme allows the user to perform a simulation again by shifting the position of the prediction target region 207 under the same simulation conditions.

In step S22, a correction effective distance can be set. As described above, a correction effective distance defines the distance from the boundary 208 of the prediction target region 207 as a target range (threshold) for the correction of the volume of each specific droplet 209. The specific droplet 209 at a distance from the boundary 208 of the prediction target region 207 which is less than the correction effective distance is subjected to volume correction. The user can set a correction effective distance by inputting a value to the input field 303*b* while referring to the Voronoi diagram. As a value input as a correction effective distance, the user can arbitrarily set, for example, a half value of the representative length of the droplet spread distribution 302 (Voronoi cell) or a minimum grid. Note that the representative length can be an arbitrary width of the spread distribution 302 (Voronoi cell) and, for example, the maximum width of the spread distribution 302 (for example, a diagonal line). Increases/decreases in the film thickness (droplet density) of the curable composition IM occur near the boundary 208. Accordingly, in consideration of a computation cost (computation time, computation load, and the like), a correction effective distance is preferably set such that only several droplets 209 near the boundary 208 fall within the correction effective distance.

In step S23, the information processing apparatus 1 obtains an index indicating the positional relationship between the boundary 208 of the prediction target region 207 and each specific droplet 209 for each of the plurality of specific droplets 209 arranged inside the prediction target region 207. In this embodiment, the information processing apparatus 1 obtains, as an index, the positional relationship between the spread distribution 302 (Voronoi cell) of the droplet 209 and the boundary 208 of the prediction target region 207. In step S24, the information processing apparatus 1 determines the volume of each specific droplet 209 (to be sometimes referred to as a simulation volume hereinafter) to be used for the simulation in step S25 based on the index obtained in step S23. For example, the information processing apparatus 1 can determine a simulation volume by multiplying the initial volume of each specific droplet 209 set in advance by the ratio of the area of a target distribution to the area of the spread distribution. The target distribution can be a range in which one specific droplet 209 inside the prediction target region 207 should spread, that is, a range in which one specific droplet 209 is in charge of spreading.

In the simulation method according to this embodiment, as described above, of the plurality of droplets 209 arranged on the shot region SR, the plurality of specific droplets 209 arranged inside the prediction target region 207 are subjected to behavior computation (prediction) in a film forming process. That is, the droplets 209 outside the prediction target region 207 with respect to the boundary 208 of the prediction target region 207 are excluded from the computation targets. In this case, the plurality of droplets 209 inside the prediction target region 207 differ in the influence of a computation model with respect to the boundary 208 in accordance with the distance from the boundary 208 of the prediction target region 207. This sometimes leads to a simulation result like increases in film thickness (droplet density) of the curable composition IM near the boundary 208 of the prediction target region 207, thus making the user have false recognition. For example, referring to FIG. 3, a boundary 208*a* on the +Y direction side and a boundary 208*b* on the −Y direction side of the prediction target region 207 differ in distance (shortest distance) to the droplets 209, and hence the droplets 209 near the boundaries 208*a* and 208*b* differ in tendency of increases/decreases in the film thickness (droplet density) of the curable composition IM. The following description will exemplify a group of specific droplets 209 (first droplet group 304) arranged near the boundary 208*a* and a group of specific droplets 209 (second droplet group 305) arranged near the boundary 208*b*.

Figure 6A:
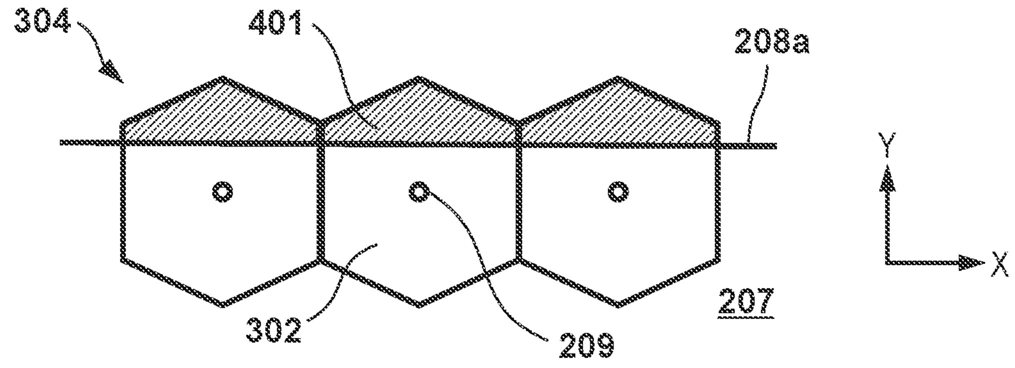
FIGS. 6A and 6B are views each showing the spread distributions of specific droplets arranged near a boundary of a prediction target region.

FIG. 6A shows the spread distribution 302 (Voronoi cell) of each specific droplet 209 in the first droplet group 304. In the first droplet group 304, as shown in FIG. 6A, the boundary 208*a* passes through the inside of the spread distribution 302 of each specific droplet 209, and the portion outside the prediction target region 207 with respect to the boundary 208*a* (on the +Y direction side from the boundary 208*a*) is excluded from the computation targets. That is, the portion (the hatched portion in FIG. 6A) of the spread distribution 302 which is located outside the prediction target region 207 is the portion in which the specific droplet 209 is assumed not to spread by a computation model for the boundary 208*a*. Accordingly, when this portion is referred to as an exclusion range 401, each specific droplet 209 in the first droplet group 304 can only spread to the range obtained by subtracting the exclusion range 401 from the spread distribution 302. For this reason, if the initial volume set in advance is used without any change as the simulation volume of each specific droplet 209, a simulation result is obtained which exhibits a local and unnatural increase in film thickness (droplet density) near the boundary 208*a*. The local increase in film thickness (droplet density) in such a simulation result may be understood as a computation error. In this case, the user may recognize a local increase in film thickness in the simulation result as the extrusion of the curable composition IM from the shot region SR (pattern region PR). The user may also recognize that the supply amount of the curable composition IM near the boundary 208*a* was too large.

Figure 6B:
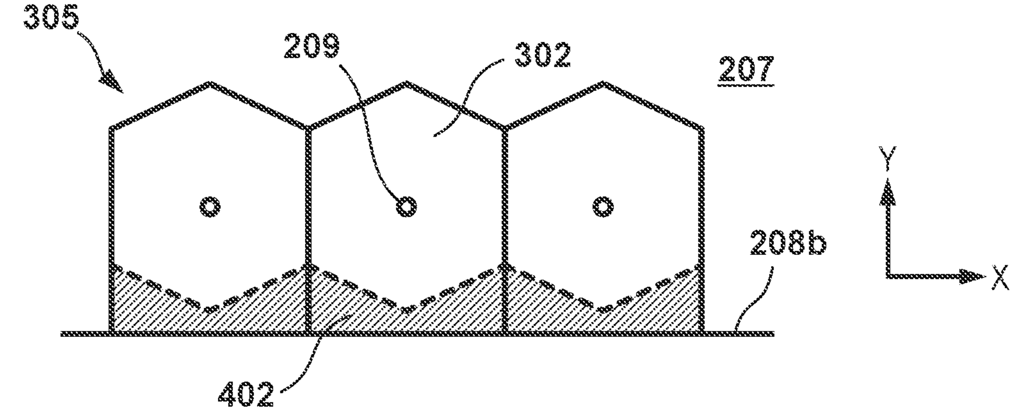

FIG. 6B shows the spread distribution 302 (Voronoi cell) of each specific droplet 209 in the second droplet group 305. In the second droplet group 305, as shown in FIG. 6B, the boundary 208*b* passes through the outside of the spread distribution 302 of each specific droplet 209. In addition, since the droplets 209 arranged outside the prediction target region 207 (on the −Y direction side from the boundary 208*a*) are excluded from the computation targets, no consideration is given to the inflow (spread) of the curable composition IM from the outside to the inside of the prediction target region 207. That is, the portion (the hatched portion in FIG. 6B) located outside the spread distribution 302 and inside the prediction target region 207 is the portion of the second droplet group 305 which should be compensated by each specific droplet 209. Accordingly, when this portion is referred to as an addition range 402, each specific droplet 209 in the second droplet group 305 needs to spread to the range obtained by adding the addition range 402 to the spread distribution 302. For this reason, if the initial volume set in advance is used without any change as the simulation volume of each specific droplet 209, a simulation result is obtained which exhibits a local and unnatural decrease in film thickness (droplet density) near the boundary 208*b*. The local decrease in film thickness (droplet density) in such a simulation result may be understood as a computation error. In this case, the user may recognize a local decrease in film thickness in the simulation result as the poor filling property of the curable composition IM to the concave portion of the pattern region PR of the mold M. The user may also recognize that the supply amount of the curable composition IM near the boundary 208*a* was too small.

As described above, the specific droplet 209 arranged near the boundary 208 of the prediction target region 207 sometimes leads to a simulation result (computation result) including a computation error that causes the false recognition of the user due to the influence of a computation model for the boundary 208. This can be caused by a change in film thickness (droplet density) near the boundary 208 of the prediction target region 207 and hence can be understood as a problem (computation error) caused by the specific droplets 209 in a limited range near the boundary 208. For this reason, in this embodiment, the ratio of the area of a target distribution to the area of the spread distribution 302 is obtained as a correction coefficient, and each specific droplet 209 is corrected by multiplying the initial volume of each specific droplet 209 set in advance by the correction coefficient, thereby obtaining the simulation volume of each specific droplet 209.

A correction coefficient can be obtained according to equation (1) using the area of the spread distribution 302 (for example, the Voronoi cell) of the specific droplet 209 as a correction target and the area of a target distribution. The target distribution is the range in which each specific droplet 209 should spread inside the prediction target region 207. As shown in FIG. 6A, the range obtained by subtracting the exclusion range 401 from the spread distribution 302 can be applied as a target distribution to each specific droplet 209 of the first droplet group 304. In contrast to this, as shown in FIG. 6B, the range obtained by adding the addition range 402 to the spread distribution 302 can be applied as a target distribution to each specific droplet 209 of the second droplet group 305. Whether the spread distribution 302 of each specific droplet 209 has the exclusion range 401 or the addition range 402 can be determined whether the boundary

208 passes through the inside of the spread distribution 302 of the specific droplet 209 nearest to the boundary 208 of the prediction target region 207.

correction coefficient=area of target distribution/area of spread distribution (1)

A simulation volume can be obtained by multiplying the initial volume set in advance for each specific droplet 209 by a correction coefficient. Since the correction coefficient is calculated inherently (individually) for each specific droplet 209 arranged inside the prediction target region 207, a simulation volume can also be calculated inherently (individually) for each specific droplet 209.

simulation volume=initial volume×correction coefficient (2)

As described above, the simulation method according to this embodiment determines a simulation volume by using the positional relationship between a spread distribution and the boundary 208 of the prediction target region 207 as an index for each of the plurality of specific droplets 209 arranged inside the prediction target region 207. This makes it possible to reduce the frequency of obtaining a simulation result that leads to false recognition by the user, for example, local increases/decreases in the film thickness (droplet density) of the curable composition IM near the boundary 208 of the prediction target region 207.

Note that in a simulation method that does not use the above processing according to this embodiment, the film thickness (droplet density) of the curable composition IM near the boundary 208 of the prediction target region 207 sometimes changes. The influence of a change in droplet density reduces the computation accuracy around the boundary 208. In addition, the reduction in computation accuracy around the boundary 208 sometimes affects the central portion of the prediction target region 207. More specifically, the thickness of a liquid film, the extrusion amount, or the like changes. In contrast to this, performing a simulation upon adjusting (correcting) the volume of each specific droplet 209 near the boundary 208 as in the above processing according to this embodiment makes it possible to obtain a good simulation result upon reduction in the influence of a change in the film thickness (droplet density) of the curable composition IM.

Second Embodiment

The second embodiment of the present invention will be described. The first embodiment has exemplified the example of obtaining the spread distribution of each droplet 209 by obtaining a Voronoi diagram in step S23. The second embodiment will exemplify a case in which in step S23, the spread distribution of each droplet 209 is obtained based on the interval between a substrate S and a mold M when the plurality of droplets 209 on the substrate S and the mold M are brought into contact with each other in a film forming process. Note that this embodiment basically inherits the first embodiment and is the same as the first embodiment except for the following particulars (for example, the manner of obtaining the spread distribution of each droplet 209).

Figure 7:
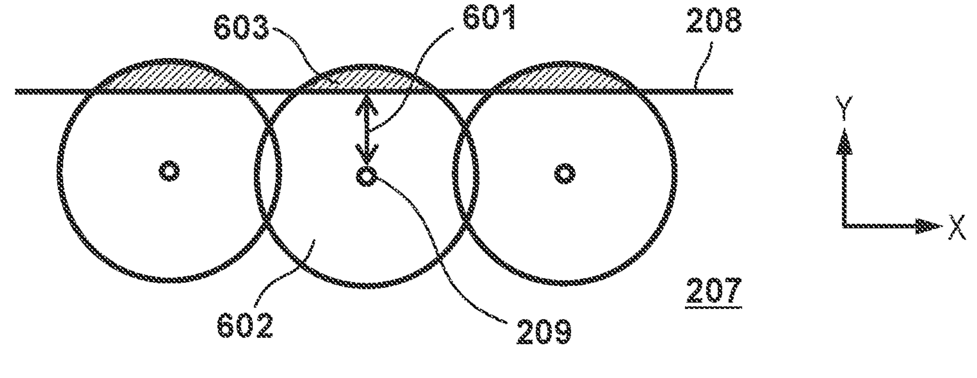
FIG. 7 is a view showing the spread distributions of specific droplets arranged near a boundary of a prediction target region.

FIG. 7 shows a spread distribution 602 (a distribution indicating the tentative spread of each droplet in a film forming process) of each specific droplet 209 arranged near a boundary 208 of a prediction target region 207. Referring to FIG. 7, the portion of the prediction target region 207 which is located on the −Y direction side with respect to the boundary 208 is defined as the inside, and the portion of the prediction target region 207 which is located on the +Y direction side is defined as the outside. In this embodiment, the spread distribution 602 indicates the range in which each specific droplet 209 spreads without consideration of the influences of other droplets when the substrate S and the mold M are brought near each other to bring the mold M into contact with the plurality of droplets 209 on the substrate S in a film forming process. The spread distribution 602 can be calculated based on the interval between the substrate S and the mold M at the time of this contact. Assuming that each specific droplet 209 spreads concentrically from its center, the spread distribution 602 of each specific droplet 209 can be calculated based on the initial volume of each specific droplet 209 set in advance and the interval between the substrate S and the mold M. For example, the spread distribution 602 can be calculated from the target film thickness of the curable composition IM by approximating the shape of the specific droplet 209 pressed by the mold M with a cylindrical column. The computation cost for computing the spread distribution 602 is smaller than the computation cost for the simulation in step S13 described above. The spread distribution 602 may be obtained by computation or simulation.

In the case shown in FIG. 7, the boundary 208 passes through the inside of the spread distribution 602 of each specific droplet 209, and the portion of the prediction target region 207 which is located outside the boundary 208 (on the +Y direction side of the boundary 208 in FIG. 7) is excluded from the computation targets. That is, the portion of the spread distribution 602 which is located outside the prediction target region 207 (the hatched portion in FIG. 7) is a portion in which the specific droplet 209 is assumed not to spread due to a computation model for the boundary 208 in a simulation. Accordingly, in the case shown in FIG. 7, when this portion is referred to as an exclusion range 603, the range obtained by subtracting the exclusion range 603 from the spread distribution 602 is applied as a target distribution, and the simulation volume of the specific droplet 209 can be obtained by using equations (1) and (2).

Obtaining the spread distribution 602 of each specific droplet 209 in this manner can be disadvantageous over obtaining the spread distribution 302 using a Voronoi diagram in terms of computation accuracy but can be advantageous in terms of computation cost. Note that when the boundary 208 passes through the outside of the spread distribution 602 of each specific droplet 209, a simulation volume is obtained in the same manner as described above only except that the spread distribution 302 in FIG. 6B is replaced with the spread distribution 602 according to this embodiment.

In this embodiment, it is difficult to compute a correction coefficient when the radius of the spread distribution 602 is exceeded. Accordingly, any specific droplet 209 that does not allow computation of a correction coefficient needs to be automatically excluded from the correction targets. In addition, since no consideration of the influences of other droplets is given to the diameter of the spread distribution 602, the representative length of the spread distribution 602 is longer than the representative length of the spread distribution 302 using a Voronoi diagram. Accordingly, since the film thickness (droplet density) of the curable composition IM is corrected in a decreasing direction, the effect of improving the computation accuracy is lower than that in the first embodiment. However, this embodiment can be said to be an effective technique when attention is given to evaluation concerning an extrusion state at the time of filling and it is desired to suppress the computation cost. The following are the reasons for this. Assume that when extrusion is to be evaluated, this embodiment is not applied to the corresponding computation. In this case, a simulation result is obtained which indicates local increases in the film thickness (droplet density) of the curable composition IM near the boundary 208*a*, and the user may erroneously recognize that extrusion begins in the corresponding portion. This can give erroneous information concerning the simulation to the user and may lead to erroneous evaluation of the result. In contrast to this, it is expected for the computation technique to which this embodiment is applied to obtain the effect of suppressing such excessive extrusion estimation. In addition, as compared with the first embodiment, the computation cost in the step of computing a droplet spread distribution is advantageously low. In a simulation, the user may select effective correction contents in accordance with the contents of calculation.

Third Embodiment

The third embodiment of the present invention will be described. In the first and second embodiments, a simulation volume is determined by using the positional relationship between the spread distribution of each specific droplet 209 and the boundary 208 of the prediction target region 207 as an index. The third embodiment will exemplify a case in which a simulation volume is determined by using the distance between each specific droplet 209 and the boundary of a prediction target region 207 as an index. Note that this embodiment basically inherits the first embodiment and is the same as the first embodiment except for the following particulars.

In this embodiment, the distance to a boundary 208 of the prediction target region 207 is obtained as an index with respect to each of the plurality of specific droplets 209 arranged inside the prediction target region 207 in step S23 in FIG. 5 described above. For example, as shown in FIG. 7, a shortest distance 601 between the specific droplet 209 and the boundary 208 can be obtained as the distance to the boundary 208. In step S24 in FIG. 5, the simulation volume of each specific droplet 209 is determined based on the index (distance) obtained in step S23. For example, in step S24, a simulation volume can be determined in accordance with the distance to the boundary 208 so as to decrease with a decrease in the distance as an index value.

In step S24 in FIG. 5, the simulation volume may be determined to be zero for each specific droplet 209, of the plurality of specific droplets 209, whose distance to the boundary 208 as the index is less than a threshold. The threshold can be arbitrarily set. The correction effective distance set by the user on an input window 303 (input field 303*b*) of a setting screen 200*b* shown in FIG. 3 may be used as the threshold. That is, the simulation volume may be determined to be zero for each specific droplet 209, of the plurality of specific droplets 209, whose distance to the boundary 208 is shorter than the correction effective distance. It can be expected that uniformly determining the simulation volumes of the specific droplets 209 whose distances to the boundary 208 are less than the threshold to be zero will further reduce the computation cost even through the computation accuracy decreases. In addition, this can reduce the frequency of obtaining a simulation result that leads to false recognition by the user, such as excessive extrusion estimation.

For the sake of descriptive convenience, the first to third embodiments each have exemplified the model (target boundary) for computing the spread of each droplet 209 to the outside of the prediction target region 207 as the spread of the droplet 209 which reverses at the boundary 208 of the prediction target region 207 and spreads inside the prediction target region 207. However, the boundary 208 is not limited to the model described here. More specifically, similar effects can be obtained with models such as a pressure boundary, a target boundary, a speed boundary, and a wall boundary which are general boundary conditions used for numerical computation.

Fourth Embodiment

The above embodiments each have exemplified the case in which the information processing apparatus 1 (simulation apparatus) that predicts the behavior of the curable composition IM in a film forming process is configured separately from the film forming apparatus IMP. However, the present invention is not limited to this, and an information processing apparatus 1 (simulation apparatus) may be incorporated in a film forming apparatus IMP. In this case, the film forming apparatus IMP can control the process of bringing the curable composition arranged on a first member into contact with a second member and forming a film of the curable composition on the first member based on the prediction of the behavior of the curable composition by the information processing apparatus 1. The above embodiments each have exemplified the form in which the mold M has a pattern. However, the present invention can also be applied to a form in which the substrate S has a pattern.

Fifth Embodiment

The fifth embodiment of the present invention will be described. The first and second embodiments each have exemplified the method of reducing the influences of the thickness of a liquid film and extrusion by adjusting the volume of each specific droplet 209. However, increasing/decreasing the volume of such a droplet will cause an error in the joining timing with another adjacent droplet. For example, a droplet with an increased volume increases in area when it is pressed flat by a mold, and hence the joining timing with an adjacent droplet quickens. Accordingly, the fifth embodiment will exemplify a method of adjusting the joining timing between droplets after the volume of each droplet is adjusted according to the first and second embodiments. The fifth embodiment will be described with reference to the first embodiment using a Voronoi diagram. Note that the fifth embodiment basically inherits the first embodiment and is the same as the first embodiment except for the following particulars.

Figure 8A:
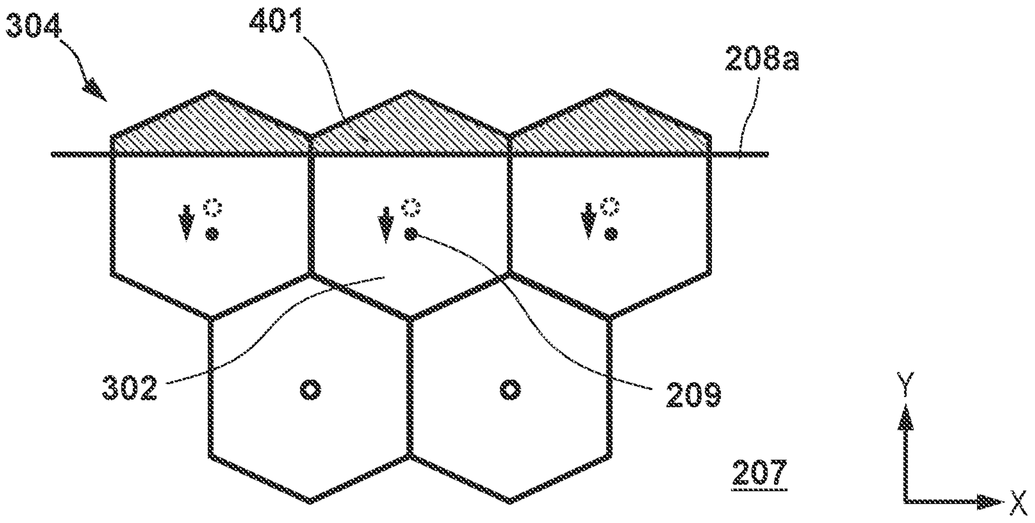
FIGS. 8A and 8B are views each showing the spread distribution of specific droplets arranged near a boundary of a prediction target region.
Figure 8B:
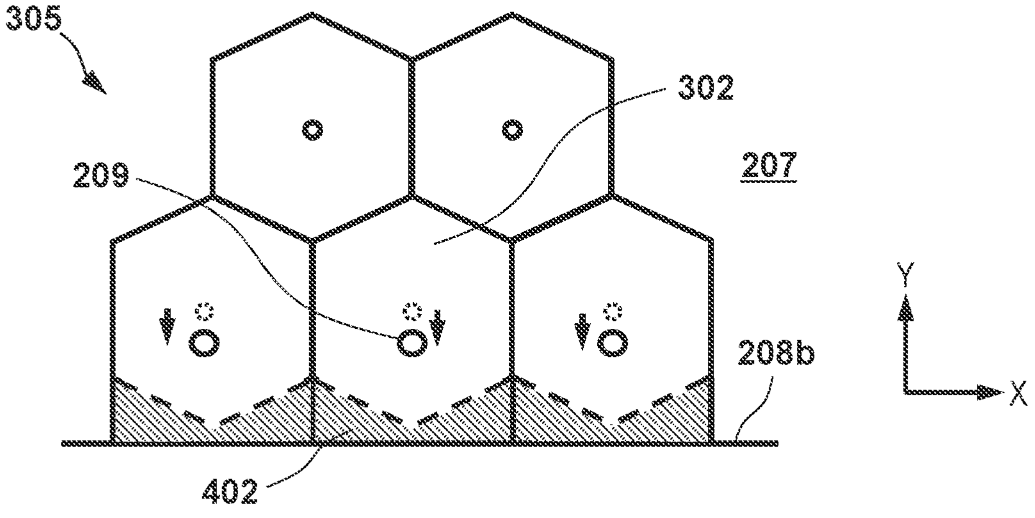

FIGS. 8A and 8B are views showing changes in the positions of specific droplets arranged near the boundary of a prediction target region. FIG. 8A shows specific droplets 209 near a boundary 208*a*. FIG. 8A shows a case in which the boundary 208*a* passes through the Voronoi cell of the specific droplet 209, and the area of a target distribution decreases with respect to the area of a spread distribution. In such a case, when the volume of the specific droplet 209 is adjusted so as to decrease, the spread of the droplet is slowed when pressed due to a decrease in volume, resulting in delaying the joining timing with an adjacent droplet. Accordingly, in this embodiment, the position of the specific droplet 209 is shifted to the position of the center of gravity of the target distribution. This moves the position of the specific droplet 209 in a direction (−Y direction) away from the boundary 208*a* and brings the droplet near another droplet whose volume is not adjusted, and hence can reduce the delay of the joining timing between the droplets.

FIG. 8B shows the specific droplet 209 near a boundary 208*b*. FIG. 8B shows a case in which the boundary 208*a* passes through the outside of the Voronoi cell of the specific droplet 209, and the area of the target distribution increases with respect to the area of the spread distribution. In such a case, when the volume of the specific droplet 209 is adjusted so as to increase, the spread of the droplet is quickened when pressed due to an increase in volume, resulting in quickening the joining timing with an adjacent droplet. Similarly, in this case, the position of the specific droplet 209 is shifted to the position of the center of gravity of the target distribution. This moves the position of the specific droplet in a direction (−Y direction) to approach the boundary 208*b* and brings the droplet away from another droplet whose volume is not adjusted, and hence can reduce the quickening of the joining timing between the droplets.

In this case, for the sake of simplicity, this embodiment has exemplified the case in which the variation of the position of the center of gravity of the target distribution is limited to one direction (the Y-axis direction in the embodiment). That is, the position of the center of gravity is sometimes changed in two directions (an X-axis direction component and a Y-axis direction component). For example, when a prediction target region 207 is rectangular, the specific droplet 209 nearest to a corner portion of the region is associated with a boundary parallel to the X-axis direction and a boundary parallel to the Y-axis direction. Accordingly, the target distribution sometimes increases/decreases in the two directions (the X-axis direction and the Y-axis direction). In this case, the position of the specific droplet 209 can also move in the two directions (the X-axis direction and the Y-axis direction) components.

As described in the first embodiment, in the second embodiment as well, the range obtained by subtracting an exclusion range 603 from a spread distribution 602 is set as a target distribution, and similar effects are obtained by shifting the position of the specific droplet 209 to the center of gravity of the target distribution.

As described above, applying this embodiment makes it possible to reduce the shift of the liquid contact timing between droplets which occurs after volume adjustment. This can reduce the frequency of obtaining a simulation result that leads to false recognition by the user.

Sixth Embodiment

The sixth embodiment of the present invention will be described. This embodiment will exemplify a case in which a droplet spread boundary enters a computation region 207. The droplet spread boundary indicates the boundary of a region in which a film of a curable composition IM should be formed by pressing a mold M. When a liquid film is to be formed near the central portion of a substrate S, since a liquid film is formed by using the entire surface of a pattern region PR (full field), a boundary portion of the pattern region PR is a liquid spread boundary. When a liquid film is to be formed near an end portion of the substrate S (partial field), a boundary portion of the pattern region PR and an outer peripheral portion of the substrate S serve as a droplet spread boundary. For the sake of simplicity, this embodiment will be described assuming that the boundary portion of the pattern region PR has a rectangle shape composed of straight lines, and the outer peripheral portion of the substrate S has a circular shape. The sixth embodiment will be described with reference to the first embodiment using a Voronoi diagram. Note that the sixth embodiment basically inherits the first embodiment and is the same as the first embodiment except for the following particulars.

Figure 9A:
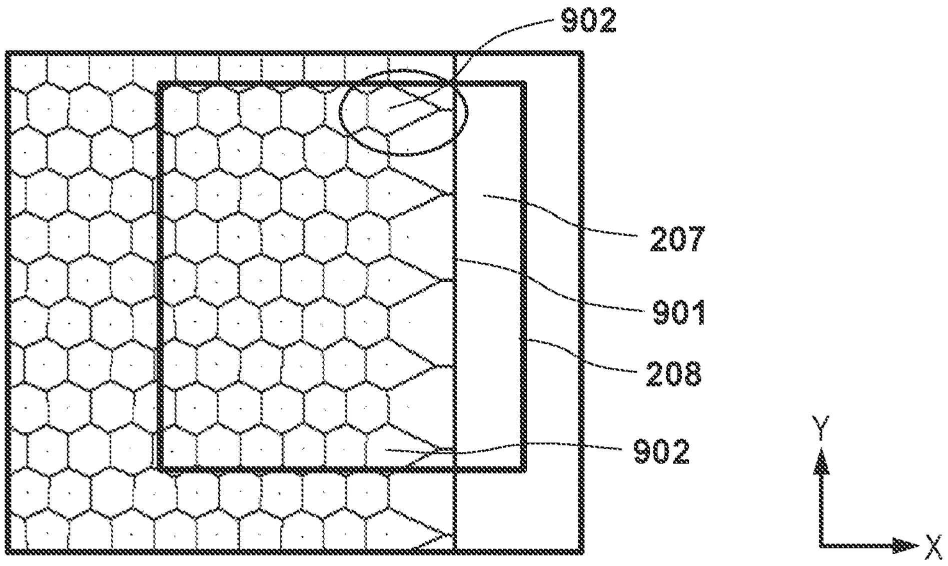
FIGS. 9A and 9B are views for explaining a case in which a droplet spread boundary formed by a pattern region is included in a prediction target region.
Figure 9B:
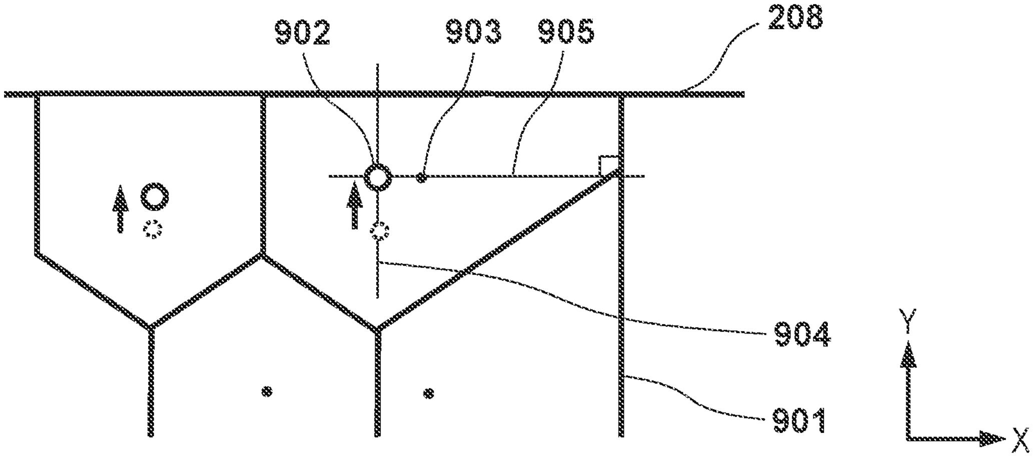

FIGS. 9A and 9B each show a case in which the droplet spread boundary originating from a shot region SR is included in the prediction target region 207. FIG. 9A shows a portion near the prediction target region. The prediction target region 207 is defined so as to include a portion of the boundary of the shot region SR which is parallel to the Y-axis direction. Accordingly, a droplet spread boundary 901 is arranged parallel to the Y-axis direction with respect to the prediction target region 207. A plurality of droplets of the curable composition IM are arranged on the side of the droplet spread boundary 901 which is located in the −X direction. No droplets of the curable composition IM are arranged on the side in the +X direction. In an actual imprint operation, "extrusion" can occur, that is, the curable composition outflows outward over the boundary 901. However, assume that when a target distribution is obtained in this embodiment, droplets of the curable composition do not spread over the boundary 901.

The simulation volume and position of each droplet when the target distribution comes into contact with the droplet spread boundary 901 greatly influence extrusion from the boundary 901. Therefore, the simulation volume and the position described above should not include in the correction target. In contrast to this, when the target distribution comes into contact with the droplet spread boundary 901 and droplets come into contact with a boundary 208 of a prediction target region, the simulation volume of each droplet is too small or large, resulting in increases/decreases in the liquid film thickness of the corresponding portion or a deterioration in the prediction accuracy of an extrusion amount. Accordingly, the simulation volume and position of each droplet need to be corrected. Assume that the droplets located at the two ends of the plurality of droplets in contact with the droplet spread boundary 901 are end droplets 902. There are two end droplets 902 in this embodiment, and a correction method for the simulation volume of each droplet is performed according to the first embodiment. Accordingly, a description of the method will be omitted.

Described next is a case in which the positions of the end droplets 902 are corrected after the volume correction described in the fifth embodiment. FIG. 9B shows the target distribution of the end droplet 902 which is surrounded by the circle in FIG. 9A. This target distribution is larger in area than the spread distribution 302, and hence the simulation volume is corrected in an increasing direction.

Droplets near the droplet spread boundary 901 are often intentionally arranged at distances from the droplet spread boundary 901 to prevent extrusion. For this reason, when a center of gravity 903 of the target distribution of the end droplet 902 is viewed, the center of gravity 903 tends to be located at a position nearer to the droplet spread boundary 901 than the initial droplet arrangement. Accordingly, when the position of each end droplet 902 is corrected as in the fifth embodiment, extrusion larger than actuality is computed, resulting in false recognition of a computation result.

In order to prevent this phenomenon, droplet position correction is not performed in a direction irrelevant to increases/decreases in the area of a target distribution (a direction intersecting at a right angle with the droplet spread boundary 901), and droplet position correction is performed in a direction relevant increases/decreases in the area of a target distribution (a direction intersecting at a right angle with the boundary 208). Assume that a line extending parallel to the droplet spread boundary 901 from the center of the end droplet 902 is a first auxiliary line 904. As long as the end droplet 902 moves on the first auxiliary line 904, the distance from the droplet spread boundary 901 does not change. On the other hand, assume that a line perpendicular to the droplet spread boundary 901 which passes through the center of gravity 903 obtained from the target distribution is a second auxiliary line 905. Moving the end droplet 902 to the intersection point between the first auxiliary line 904 and the second auxiliary line 905 can correct the position while keeping the distance from the droplet spread boundary in the normal direction. In this case, when the simulation volume and droplet position of a droplet adjacent left (−X direction) to the end droplet 902 are corrected, since the droplet is not in contact with the droplet spread boundary, the correction is performed according to the first embodiment.

Figure 10A:
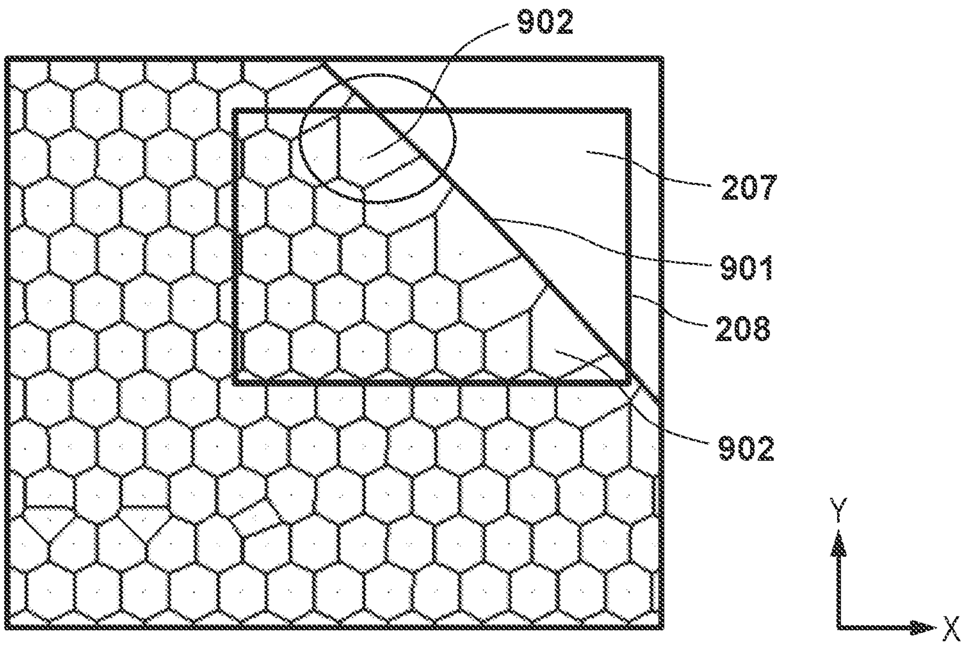
FIGS. 10A and 10B are views for explaining a case in which a droplet spread boundary formed by an end portion of a substrate is included in a prediction target region.
Figure 10B:
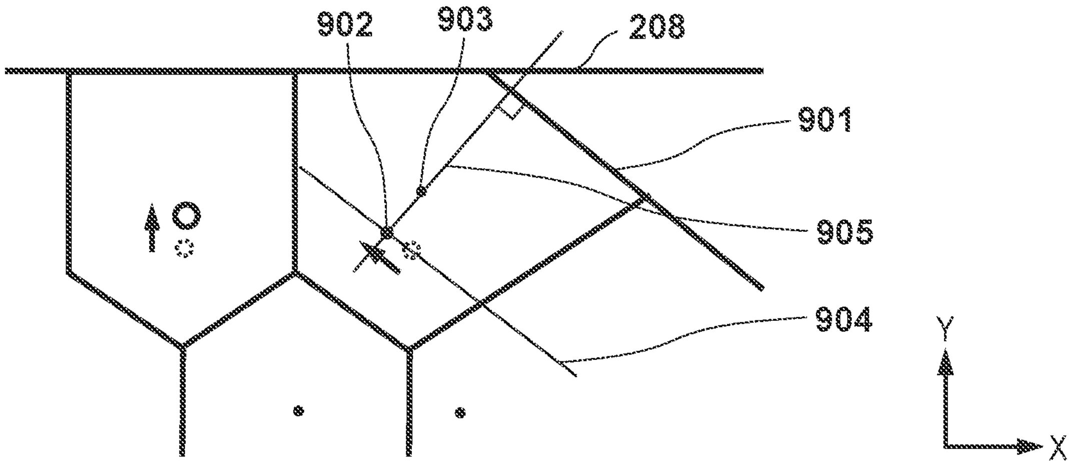

FIGS. 10A and 10B each show a case in which the droplet spread boundary 901 defined by end portions of the substrate S is included in the prediction target region 207. FIG. 10A shows a portion near the prediction target region. In the case of the pattern region PR, the droplet spread boundary 901 is composed of a straight line. In this case, however, the droplet spread region is composed of a curved line.

In the case shown in FIGS. 10A and 10B as well, a plurality of droplets of the curable composition IM are arranged in the lower left direction corresponding to the inside of the substrate S with respect to the droplet spread boundary 901. On the other hand, no droplets of the curable composition IM are arranged in the upper right direction corresponding to the outside of the substrate S. In the case shown in FIGS. 10A and 10B as well, assume that when a target distribution is obtained, any droplets of a curable composition do not spread over the boundary 901.

In the case shown in FIGS. 10A and 10B, as in the description with reference to FIGS. 9A and 9B, the simulation volume and position of any droplet in contact with the droplet spread boundary 901 should not be included in the correction targets. The end droplets 902 in contact with the droplet spread boundary 901 and the boundary 208 of the prediction target region require correction of the simulation volumes and positions of the droplets. In the case shown in FIGS. 10A and 10B, there are two droplets 902, and a simulation volume correction method for each droplet is performed according to the first embodiment. Accordingly, a description of the method will be omitted.

Described next is a case in which position correction for the end droplets 902 is performed after the volume correction described in the fifth embodiment. FIG. 10B shows the target distribution of the end droplet 902 which is surrounded by the circle in FIG. 10A. Since this target distribution is smaller in area than the spread distribution 302, the simulation volume is corrected in a decreasing direction.

Assume that a curve extending parallel to the droplet spread boundary 901 from the center of the end droplet 902 is the first auxiliary line 904. As long as the end droplet 902 moves on the first auxiliary line 904, the distance from the droplet spread boundary 901 does not change. On the other hand, assume that a normal line of the droplet spread boundary 901 which passes through the center of gravity 903 obtained from the target distribution is the second auxiliary line 905. Moving the position of the end droplet 902 to the intersection point between the first auxiliary line 904 and the second auxiliary line 905 can correct the position while keeping the distance from the droplet spread boundary in the normal direction. In this case shown in FIGS. 10A and 10B as well, when the simulation volume and droplet position of a droplet adjacent left (−X direction) to the end droplet 902 are corrected, since the droplet is not in contact with the droplet spread boundary, the correction is performed according to the first embodiment.

As described above, applying this embodiment makes it possible to reduce the shift of the liquid contact timing between droplets which occurs after volume adjustment even if a droplet spread boundary is included in a prediction target region. This can reduce the frequency of obtaining a simulation result that leads to false recognition by the user.

Embodiment of Method of Manufacturing Article

A method of manufacturing an article according to an embodiment can include a step of determining conditions for a film forming process based on the result obtained by executing the above simulation method and a step of executing the film forming process according to the conditions. In the step of determining conditions for a film forming process, conditions for the film forming process may be determined while the simulation method is repeated.

FIGS. 11A to 11F show a more detailed example of the method of manufacturing an article. As shown FIG. 11A, a substrate 1*z* such as a silicon wafer with a processed material 2*z* such as an insulator formed on the surface is prepared. Next, an imprint material 3*z* is applied to the surface of the processed material 2*z* by an inkjet method or the like. A state in which the imprint material 3*z* is applied as a plurality of droplets onto the substrate is shown here.

Figure 11A:
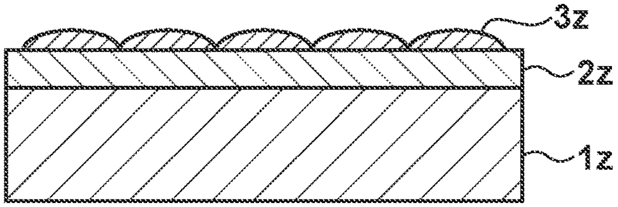
FIGS. 11A to 11F are sectional views for explaining a method of manufacturing an article.
Figure 11B:
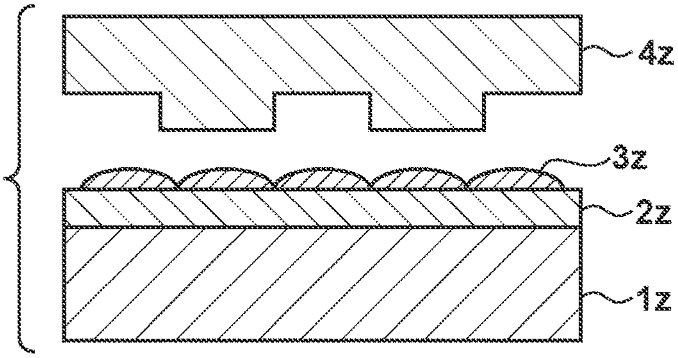
Figure 11C:
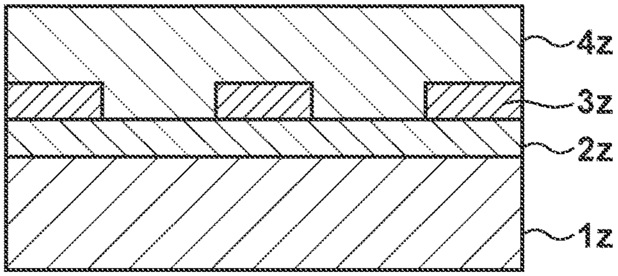

As shown in FIG. 11B, a side of a mold 4*z* for imprint with a concave-convex pattern is directed toward and made to face the imprint material 3*z* on the substrate. As shown FIG. 11C, the substrate 1*z* to which the imprint material 3*z* is applied is brought into contact with the mold 4*z*, and a pressure is applied. The gap between the mold 4*z* and the processed material 2*z* is filled with the imprint material 3*z*. In this state, when the imprint material 3*z* is irradiated with light as energy for curing via the mold 4*z*, the imprint material 3*z* is cured.

Figure 11D:
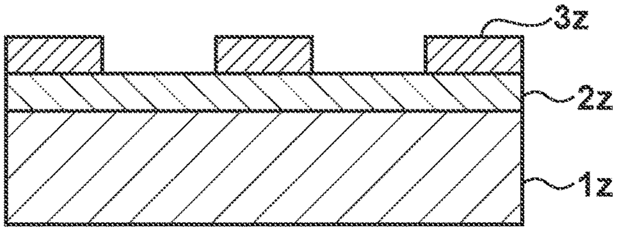

As shown in FIG. 11D, after the imprint material 3*z* is cured, the mold 4*z* is separated from the substrate 1*z*, and the pattern of the cured product of the imprint material 3*z* is formed on the substrate 1*z*. In the pattern of the cured product, the concave portion of the mold corresponds to the convex portion of the cured product, and the convex portion of the mold corresponds to the concave portion of the cured product. That is, the concave-convex pattern of the mold 4*z* is transferred to the imprint material 3*z*.

Figure 11E:
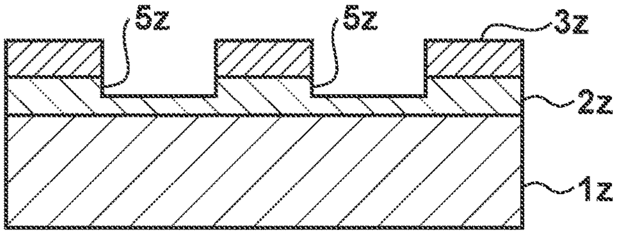
Figure 11F:
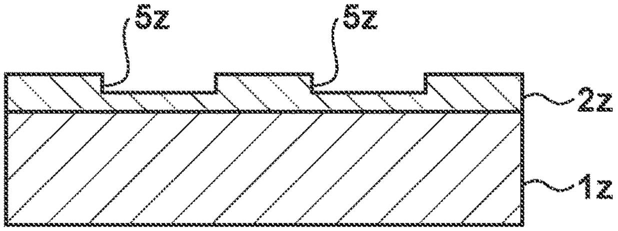

As shown in FIG. 11E, when etching is performed using the pattern of the cured product as an etching resistant mask, a portion of the surface of the processed material 2*z* where the cured product does not exist or remains thin is removed to form grooves 5*z*. As shown in FIG. 11F, when the pattern of the cured product is removed, an article with the grooves 5*z* formed in the surface of the processed material 2*z* can be obtained. Here, the pattern of the cured product is removed. However, instead of removing the pattern of the cured product after the process, it may be used as, for example, an interlayer dielectric film included in a semiconductor element or the like, that is, a constituent member of an article.

Other Embodiments

Embodiment(s) of the present invention can also be realized by a computer of a system or apparatus that reads out and executes computer executable instructions (e.g., one or more programs) recorded on a storage medium (which may also be referred to more fully as anon-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-032586 filed on Mar. 2, 2021, and Japanese Patent Application No. 2021-201174, filed Dec. 10, 2021, which are hereby incorporated by reference herein in their entirety.

What is claimed is:

1. A method of controlling a film forming process, which includes arranging a curable composition as a plurality of droplets on a first member and bringing a second member into contact with the plurality of droplets on the first member to form a film of the curable composition between the first member and the second member, the method comprising:

simulating, by a computer with a processor and a memory, to predict a behavior of the curable composition in the film forming process, wherein the simulating includes:

setting, by the computer, a prediction target region in a part of a region of the first member on which the curable composition is arranged, the prediction target region being a computational region extracted from a partial region of a shot region for reducing computation cost in the simulating, wherein the prediction target region has a boundary that defines a limit of the computational region;

obtaining, for each of a plurality of specific droplets arranged inside the prediction target region among the plurality of droplets, a spread distribution indicating a spread of the specific droplet in the film forming process, wherein a droplet spread boundary, which is a boundary to which each of the plurality of specific droplets is allowed to spread, is included in the prediction target region; and determining, for each of the plurality of specific droplets, a target distribution based on a positional relationship among the spread distribution of the specific droplet, the boundary of the prediction target region, and the droplet spread boundary, the target distribution being a range in which the specific droplet spreads inside the prediction target region;

determining a volume used for predicting the behavior of the curable composition for each of the plurality of specific droplets by multiplying an initial volume of the specific droplet by a ratio of an area of the target distribution to an area of the spread distribution, wherein the volume is determined to reduce computation errors caused by applying a computation model that assumes each of the plurality of specific droplets does not spread outside the boundary of the prediction target region;

for a specific droplet having the target distribution in contact with both the boundary of the prediction target region and the droplet spread boundary, moving a position of the specific droplet to an intersection point between a first auxiliary line and a second auxiliary line, wherein the first auxiliary line is parallel to the droplet spread boundary and passes through the specific droplet before the moving, wherein the second auxiliary line is perpendicular to the droplet spread boundary and passes through a center of gravity of the target distribution, and wherein moving the position of the specific droplet to the intersection point maintains a distance of the specific droplet from the droplet spread boundary in a normal direction of the droplet spread boundary;

predicting the behavior of the curable composition inside the prediction target region based on the determined volume for each of the plurality of specific droplets and the moved position of the specific droplet;

determining, based on a result of the predicting, a dispense condition for a dispenser, the dispense condition including at least one of a volume and a position of a droplet to be dispensed on the first member;

controlling the dispenser according to the dispense condition to dispense the plurality of droplets on the first member;

bringing the second member into contact with the dispensed plurality of droplets on the first member to spread the curable composition between the first member and the second member; and curing the curable composition spread between the first member and the second member to form the film.

2. The method according to claim 1, wherein the plurality of droplets includes a non-correction droplet having a corresponding target distribution that is in contact with the droplet spread boundary but is not in contact with the boundary of the prediction target region, and wherein the non-correction droplet is excluded from droplets for which a volume and a position are adjusted in the simulating based on the positional relationship with the boundary of the prediction target region.

3. The method according to claim 1, wherein the spread distribution is obtained as a unit cell in a Voronoi diagram obtained by segmenting at least a region including the prediction target region using each of the plurality of droplets as a generatrix.

4. The method according to claim 1, wherein, for another specific droplet different from the specific droplet having the target distribution in contact with both the boundary of the prediction target region and the droplet spread boundary, a position of the another specific droplet whose volume has been adjusted is moved to a center of gravity of the target distribution corresponding to the another specific droplet.

5. A method of manufacturing an article, the method comprising:

simulating, by a computer with a processor and a memory, to predict a behavior of a curable composition in a film forming process, which includes arranging the curable composition as a plurality of droplets on a first member and bringing a second member into contact with the plurality of droplets on the first member to form a film of the curable composition between the first member and the second member, wherein the simulating includes:

setting, by the computer, a prediction target region in a part of a region of the first member on which the curable composition is arranged, the prediction target region being a computational region extracted from a partial region of a shot region for reducing computation cost in the simulating, wherein the prediction target region has a boundary that defines a limit of the computational region;

obtaining, for each of a plurality of specific droplets arranged inside the prediction target region among the plurality of droplets, a spread distribution indicating a spread of the specific droplet in the film forming process, wherein a droplet spread boundary, which is a boundary to which each of the plurality of specific droplets is allowed to spread, is included in the prediction target region; and determining, for each of the plurality of specific droplets, a target distribution based on a positional relationship among the spread distribution of the specific droplet, the boundary of the prediction target region, and the droplet spread boundary, the target distribution being a range in which the specific droplet spreads inside the prediction target region;

determining a volume used for predicting the behavior of the curable composition for each of the plurality of specific droplets by multiplying an initial volume of the specific droplet by a ratio of an area of the target distribution to an area of the spread distribution;

for a specific droplet having the target distribution in contact with both the boundary of the prediction target region and the droplet spread boundary, moving a position of the specific droplet to an intersection point between a first auxiliary line and a second auxiliary line, wherein the first auxiliary line is parallel to the droplet spread boundary and passes through the specific droplet before the moving, wherein the second auxiliary line is perpendicular to the droplet spread boundary and passes through a center of gravity of the target distribution;

predicting the behavior of the curable composition inside the prediction target region based on the determined volume and the moved position of the specific droplet;

determining, based on a result of the predicting, a process condition for the film forming process;

dispensing, by a dispenser, the plurality of droplets on the first member according to the process condition;

bringing the second member into contact with the dispensed plurality of droplets to spread the curable composition between the first member and the second member;

curing the curable composition to form the film on the first member; and processing the first member on which the film has been formed to manufacture the article.

* * * * *